United States Patent
Pei et al.

(10) Patent No.: US 10,668,292 B2
(45) Date of Patent: Jun. 2, 2020

(54) IMPLANTABLE MEDICAL DEVICES, AND METHODS OF USE THEREWITH, THAT DETECT MRI SYSTEMS WITH ENHANCED SPECIFICITY

(71) Applicant: Pacesetter, Inc., Santa Clara, CA (US)

(72) Inventors: Xing Pei, Thousand Oaks, CA (US); Brad Lindevig, Santa Monica, CA (US); Stuart Rosenberg, Castaic, CA (US); Nima Badie, Berkeley, CA (US)

(73) Assignee: Pacesetter, Inc., Sylmar, CA (US)

( * ) Notice: Subject to any disclaimer, the term of this patent is extended or adjusted under 35 U.S.C. 154(b) by 168 days.

(21) Appl. No.: 15/933,176

(22) Filed: Mar. 22, 2018

(65) Prior Publication Data

US 2019/0290919 A1    Sep. 26, 2019

(51) Int. Cl.
| | | |
|---|---|---|
| *A61N 1/37* | (2006.01) | |
| *A61N 1/39* | (2006.01) | |
| *A61N 1/05* | (2006.01) | |
| *A61N 1/365* | (2006.01) | |
| *G01R 33/00* | (2006.01) | |
| *A61B 5/055* | (2006.01) | |
| *G01R 33/28* | (2006.01) | |
| *G01R 33/07* | (2006.01) | |
| *G01R 33/09* | (2006.01) | |
| *A61N 1/08* | (2006.01) | |

(52) U.S. Cl.
CPC ............ *A61N 1/3718* (2013.01); *A61B 5/055* (2013.01); *A61N 1/0587* (2013.01); *A61N 1/086* (2017.08); *A61N 1/36507* (2013.01); *A61N 1/36535* (2013.01); *A61N 1/3931* (2013.01); *G01R 33/0088* (2013.01); *G01R 33/07* (2013.01); *G01R 33/093* (2013.01); *G01R 33/288* (2013.01)

(58) Field of Classification Search
CPC ... A61N 1/3718; A61N 1/086; A61N 1/36535
USPC .......................................................... 607/11
See application file for complete search history.

(56) References Cited

U.S. PATENT DOCUMENTS

| 4,686,988 A | 8/1987 | Sholder |
|---|---|---|
| 4,708,142 A | 11/1987 | DeCote, Jr. |
| 4,712,555 A | 12/1987 | Thornander et al. |

(Continued)

*Primary Examiner* — Amanda K Hulbert
*Assistant Examiner* — Philip C Edwards
(74) *Attorney, Agent, or Firm* — Vierra Magen Marcus LLP

(57) ABSTRACT

Embodiments describe herein generally pertain to implantable medical device (IMDs), and methods for use therewith, that can be used to automatically switch an IMD from its normal operational mode to an MRI safe mode, and vice versa, within increased specificity. In certain embodiments, a controller of the IMD uses a magnetic field sensor to determine whether a first magnetic field condition is detected, and uses an accelerometer to determine whether a positional condition is detected. In response to the first magnetic field condition being detected, and the positional condition being detected, the controller can use the magnetic field sensor to determine whether a second magnetic field condition is detected, which differs from the first magnetic field condition. The controller can then cause the IMD to enter the MRI safe mode based at least in part on the first and second magnetic field conditions and the positional condition being detected.

19 Claims, 6 Drawing Sheets

(56) References Cited

U.S. PATENT DOCUMENTS

| | | | |
|---|---|---|---|
| 4,729,376 | A | 3/1988 | DeCote, Jr. |
| 4,788,980 | A | 12/1988 | Mann et al. |
| 4,809,697 | A | 3/1989 | Causey, III et al. |
| 4,940,052 | A | 7/1990 | Mann et al. |
| 4,944,299 | A | 7/1990 | Silvian |
| 4,969,467 | A | 11/1990 | Callaghan et al. |
| 5,350,410 | A | 9/1994 | Kleks et al. |
| 6,101,417 | A | 8/2000 | Vogel et al. |
| 6,252,335 | B1 | 6/2001 | Nilsson et al. |
| 6,275,735 | B1 | 8/2001 | McClure et al. |
| 6,466,821 | B1 | 10/2002 | Pianca et al. |
| 6,658,292 | B2 | 12/2003 | Kroll et al. |
| 8,002,465 | B2 | 8/2011 | Ahn |
| 8,606,365 | B2 | 12/2013 | Sison |
| 8,678,430 | B2 | 3/2014 | Motomochi et al. |
| 2003/0040776 | A1* | 2/2003 | Kroll .................. A61N 1/36585 607/9 |
| 2013/0268012 | A1* | 10/2013 | Sison .................. A61N 1/3718 607/4 |

\* cited by examiner

IMPLANTABLE MEDICAL DEVICES, AND METHODS OF USE THEREWITH, THAT DETECT MRI SYSTEMS WITH ENHANCED SPECIFICITY

FIELD OF THE TECHNOLOGY

Embodiments of the present technology generally pertain to implantable medical devices, and methods for use therewith, that detect when such a device is placed within or otherwise exposed to a magnetic resonance imaging (MRI) system.

BACKGROUND

Implantable medical devices (IMDs) are implanted in patients to monitor, among other things, electrical cardiac activity, and to deliver appropriate cardiac electrical therapy, as required. IMDs include pacemakers, cardioverters, defibrillators, implantable cardioverter defibrillators (ICD), and the like. The electrical therapy produced by an IMD may include pacing pulses, cardioverting pulses, and/or defibrillator pulses to reverse arrhythmias (e.g., tachycardias and bradycardias) or to stimulate the contraction of cardiac tissue (e.g., cardiac pacing) to return the heart to its normal sinus rhythm. IMDs can also be used to perform cardiac resynchronization therapy (CRT). IMDs can alternatively, or additionally, provide for neurostimulation.

When IMDs are exposed to external magnetic fields, such as those produced by magnetic resonance imaging (MRI) systems, the magnetic fields may interfere with operation of the IMDs. For example, an MRI system can cause electromagnetic field interference with leads, electrodes, and/or other sensing circuitry of or attached to an IMD. These forces may induce electric charges or potentials on the leads and electrodes, which can cause over- or under-sensing of cardiac signals. For example, the charges may cause the electrodes and leads to convey signals to an IMD that are not cardiac signals but are treated by the IMD as cardiac signals. This may cause the IMD to falsely detect tachycardias (which do not actually exist), potentially causing the IMD to delivery anti-tachycardia pacing (ATP) or cardioversion/defibrillation shock therapy (when not actually necessary and may be pro-arrhythmic). In another example, the charges induced by MRI systems may induce sufficient noise in cardiac signals such that cardiac signals that are representative of cardiac events go undetected by an IMD. This may cause the IMD to not detect a normal sinus rhythm (which actually exists), potentially causing the IMD to delivery inappropriate pacing (when actually unnecessary and may be pro-arrhythmic). This may also cause the IMD to not deliver pacing therapy (when actually necessary), since it falsely believes there are intrinsic cardiac events ongoing.

An MRI system generally produces and utilizes three types of electromagnetic fields, which include a strong static magnetic field, a time-varying gradient magnetic field, and a radio frequency (RF) magnetic field, which can collectively be referred to as the electro-magnetic field from an MRI system. The time-varying gradient field and the RF field may be referred to as different parts of the time-varying electro-magnetic field. In other words, the time-varying gradient field and the RF field can collectively be referred to as the time-varying electro-magnetic field. The static field produced by most MRI systems has a magnetic induction ranging from about 0.35 Tesla (T) to about 4 T, but can be potentially higher (e.g., 7 T and 9 T MRI systems are sometimes used in research). More specifically, MRI systems may generate external static magnetic fields having different strengths, such as 0.35 T, 0.5 T, 0.7 T, 1.0 T, 1.2 T, 1.5 T, 3 T, 4 T etc. The RF field includes RF pulses. The frequency of the RF field is correlated to the magnitude of the static magnetic field to provide the best scanning result, with the frequency of the RF field being approximately 42.58e6*static field strength. For example, where the static magnetic field strength is 1.5 T, the RF is at 42.58e6~1.5~64 MHz; and where the static magnetic field is 3 T, the RF is at 42.58e6*3~128 MHz. The time-varying gradient magnetic field, which is used for spatial encoding, typically has a frequency in the KHz range, but for many MRI sequences can have relatively high power in the sub-KHz range.

In order to safely operate while exposed to magnetic fields produced by MRI systems, IMDs may need to switch modes to an "MRI safe mode", which is sometimes more succinctly as an "MRI mode". When in an MRI safe mode, an IMD may change the algorithms, software, and/or logical steps by which cardiac signals are monitored, and/or by which pacing and/or other cardiac therapy is delivered. For example, an IMD may change which algorithms are used to identify an arrhythmia. Alternatively, the IMD may cease measuring or sensing cardiac signals.

The normal operational mode can be the operational mode of the IMD prior to it being switched to the MRI safe mode. Thus, for cardiac rhythm management ("CRM") type IMDs, such as Brady and/or Tachy devices, for example, the normal operational mode is the CRM device's initially programmed mode. The term "MRI safe mode", as used herein, can refer to any operational mode of an IMD that is a safe operational mode in the presence of the electro-magnetic fields generated by MRI systems. For example, for a Brady device (as well as a Brady engine in a Tachy device) an MRI safe mode might be a fixed-rate and/or non-demand (or asynchronous) pacing mode for a patient that needs pacing, or can turn off pacing for a patient that is not pacer dependent, as opposed to a rate-responsive and/or demand pacing mode. In some embodiments, an MRI safe mode can be both a non-demand mode (i.e., VOO) and a non-rate-responsive mode. Thus, in accordance with one embodiment, switching a Brady device to an MRI safe mode might entail mode switching to a VOO, AOO or DOO pacing mode.

The MRI safe mode to which the IMD is switched will typically depend on the normal operational mode of the IMD. For example, an IMD whose normal operational modes is a Dxx mode (e.g., a DDDR, DDD, DDI, or DVI mode) can perform a mode switch to DOO when exposed to an electro-magnetic field generated by an MRI system (i.e., the MRI safe mode can be a DOO mode). In another embodiment, for an IMD whose normal operational mode is a Vxx mode (e.g., a VDDR, VDD, VDI, or VVI mode), the MRI safe mode can be a VOO mode. In still another embodiment, for an IMD having an Axx mode as its normal operational mode (e.g., an ADDR, ADD, ADI, or AVI mode), the MRI safe mode can be an AOO mode. These are just a few examples, which are not meant to be all encompassing.

The MRI safe mode for a Tachy device might comprise turning-off tachy detection and/or therapy, as well as switching to a fixed-rate, non-demand pacing mode. In these embodiments, turning the tachy detection off will ensure that noise which might be induced on the device leads by an MRI scan is not mistaken by the device for a tachycardia, which might result in an inappropriate anti-tachycardia pacing (ATP) or shock during an MRI. Also, for CRM devices, there may be other modes of operation that are considered safe in an MRI environment.

Once the IMD leaves or is otherwise not exposed to the strong magnetic field from an MRI system, the IMD should preferably switch back to its normal mode of operation, which is also referred to as the normal operational mode. In the normal operational mode, the IMD may resume monitoring cardiac signals as the IMD 110 did before the IMD was exposed to a strong magnetic field from an MRI system. Exemplary normal operational modes and MRI safe modes were discussed above.

An IMD's failure to switch from its normal operational mode into an MRI safe mode, when it should have, may cause the IMD to inhibit necessary pacing, or delivery unnecessarily high voltage therapy or anti-tachycardia pacing, which may induce an arrhythmia. Further, failure of an IMD to switch out of an MRI safe mode and back to its normal operational mode, when it should have, may cause pacing that leads to non-optimal therapy, loss of rate-response, pacemaker syndrome, and/or other problems, and may cause no delivery of high voltage therapy or anti-tachycardia pacing to treat an tachyarrhythmia.

Some IMDs require that a clinician send a telemetry command to the IMD, via a special external programmer, in order to put the IMD in an MRI safe mode, as well as to switch the IMD out of the MRI safe mode and back to its normal operational mode. However, the needs for this special external programmer and for clinician training on using the external programmer are time consuming, costly and cumbersome. Further, this protocol may not be properly followed, or interfere with other procedures, e.g., in emergency situations, when the technician operating the MRI system is not aware that the patient has an IMD, and/or when an appropriate external programmer is unavailable.

Some IMDs have an automatic MRI (Auto-MRI) detection capability that enables an IMD to automatically detect when the IMD is exposed to an MRI field of an MRI system, thereby enabling the IMD to switch itself into and out of an MRI safe mode. For example, such an IMD can use a magnetic field sensor to detect when a sensed magnetic field exceeds a specified threshold, and the IMD can switch itself into an MRI safe mode when the threshold is exceeded, and can switch itself out of the MRI safe mode when the threshold is no longer exceeded. Exemplary types of magnetic field sensors that can be included within an IMD and used to perform automatic MRI detection include a giant magnetoresistance (GMR) sensor, a reed switch, and a Hall effect sensor.

False positive detections of a magnetic field by a magnetic field sensor (e.g., a GMR sensor, a reed switch, or a Hall effect sensor) of an IMD may cause the IMD to inappropriately switch from its normal operational mode to its MRI safe mode. This may cause the IMD to not detect a tachycardia (which actually exists), potentially causing the IMD to not delivery appropriate anti-tachycardia pacing (ATP) or defibrillation shock therapy (when actually necessary), as well as non-optimal bradytherapy. Accordingly, inappropriately switching to the MRI safe mode may inhibit potentially life-saving defibrillation therapy.

Therefore, a need still exists for IMDs, and methods for use therewith, that can detect when an IMD is within an MRI system, preferably with increased specificity.

SUMMARY

Embodiments of the present technology generally pertain to IMDs, and methods for use therewith, wherein an IMD includes a magnetic field sensor and an accelerometer and is capable of mode switching to an MRI safe mode. The magnetic field sensor can include, for example, at least one Hall effect sensor, at least one GMR sensor, and/or at least one reed switch, but is not limited thereto. In accordance with certain embodiments, a method includes using the magnetic field sensor to determine whether a first magnetic field condition is detected. The method also includes, in response to determining that the first magnetic field condition is detected, using the accelerometer to determine whether a positional condition is detected. Further, in response to determining that the positional condition is detected, the method includes using the magnetic field sensor to determine whether a second magnetic field condition is detected, wherein the second magnetic field condition differs from the first magnetic field condition. Additionally, the method includes performing a mode switch to the MRI safe mode, based at least in part on determining that the first and second magnetic field conditions and the positional condition are detected.

In accordance with certain embodiments, the positional condition comprises the patient being supine. In accordance with other embodiments, the positional condition comprises the patient being stationary. In accordance with certain embodiments, the position condition comprises the patient being both supine and stationery.

In accordance with certain embodiments, the first magnetic field condition comprises a measured magnetic field along a first-axis (e.g., a z-axis) exceeding a first-axis threshold, and the second magnetic field condition comprises a measured magnetic field along the first-axis exceeding an increased first-axis threshold. In such an embodiment, the mode switch to the MRI safe mode can be based at least in part on determining that the measured magnetic field along the first-axis exceeds the first-axis threshold, determining that the positional condition is detected, and determining that the measured magnetic field along the first-axis exceeds the increased first-axis threshold.

In accordance with certain embodiments, the first magnetic field condition comprises a measured magnetic field along a first-axis (e.g., a z-axis) exceeding a first-axis threshold, and the second magnetic field condition comprises a measured magnetic field along a second-axis (e.g., an x-axis or y-axis), which is orthogonal to the first-axis, exceeding a second-axis threshold. In such an embodiment, the mode switch to the MRI safe mode can be based at least in part on determining that the measured magnetic field along the first-axis exceeds the first-axis threshold, determining that the positional condition is detected, and determining that the measured magnetic field along the second-axis exceeds the second-axis threshold. Also, in such an embodiment, if the measured magnetic field along the second-axis does not exceed the second-axis threshold, the magnetic field sensor can be used to determine whether a measured magnetic field along the first-axis exceeds an increased first-axis threshold. A mode switch to the MRI safe mode can then be performed based at least in part on determining that the measured magnetic field along the first-axis exceeds the first-axis threshold, determining that the positional condition is detected, and determining that the measured magnetic field along the first-axis exceeds the increased first-axis threshold.

In accordance with certain embodiments, the first magnetic field condition comprises a measured magnetic field along a first-axis (e.g., a z-axis) exceeding a first-axis threshold, and the second magnetic field condition comprises a measured magnetic field along a second-axis (e.g., an x-axis) exceeding a second-axis threshold, and a measured magnetic field along a third-axis (e.g., a y-axis) exceeding a third-axis threshold, wherein the first-, second-, and third-axes are orthogonal to one another. In such an embodiment, the mode switch to the MRI safe mode can be performed based at least in part on determining that the measured magnetic field along the first-axis exceeds the first-axis threshold, determining that the positional condition is detected, and determining that the measured magnetic fields along the second-axis and the third-axis respectively exceed the second-axis threshold and the third-axis threshold. In such an embodiment, if the measured magnetic field along the second-axis does not exceed the second-axis threshold and/or that the measured magnetic field along the third-axis does not exceed the third-axis threshold, then the magnetic field sensor can be used to determine whether a measured magnetic field along at least one of the first-, second- or third-axis exceeds a respective increased first-, second- or third-axis threshold. A mode switch to the MRI safe mode can then be performed based at least in part on determining that the measured magnetic field along the first-axis exceeds the first-axis threshold, determining that the positional condition is detected, and determining that the measured magnetic field along at least one of the first-, second- or third-axis exceeds the respective increased first-, second- or third-axis threshold.

In accordance with certain embodiments, an implantable medical device (IMD) comprises a magnetic field sensor, an accelerometer, and a controller. The accelerometer can, for example, be used to detect posture and/or motion of a patient in which the IMD including the accelerometer is implanted. The controller can be configured to use the magnetic field sensor to determine whether a first magnetic field condition is detected, and use the accelerometer to determine whether a positional condition is detected. The controller can also be configured to use the magnetic field sensor to determine whether a second magnetic field condition is detected, in response to both the first magnetic field condition being detected and the positional condition being detected, wherein the second magnetic field condition differs from the first magnetic field condition. Additionally, the controller can cause the IMD to enter an MRI safe mode based at least in part on the first and second magnetic field conditions and the positional condition being detected, as well as cause the IMD to exit an MRI safe mode when appropriate and return to its normal operational mode.

This summary is not intended to be a complete description of the technology. Other features and advantages of the technology will appear from the following description in which the preferred embodiments have been set forth in detail, in conjunction with the accompanying drawings and claims.

DETAILED DESCRIPTION OF PREFERRED EMBODIMENTS

Figure 1:
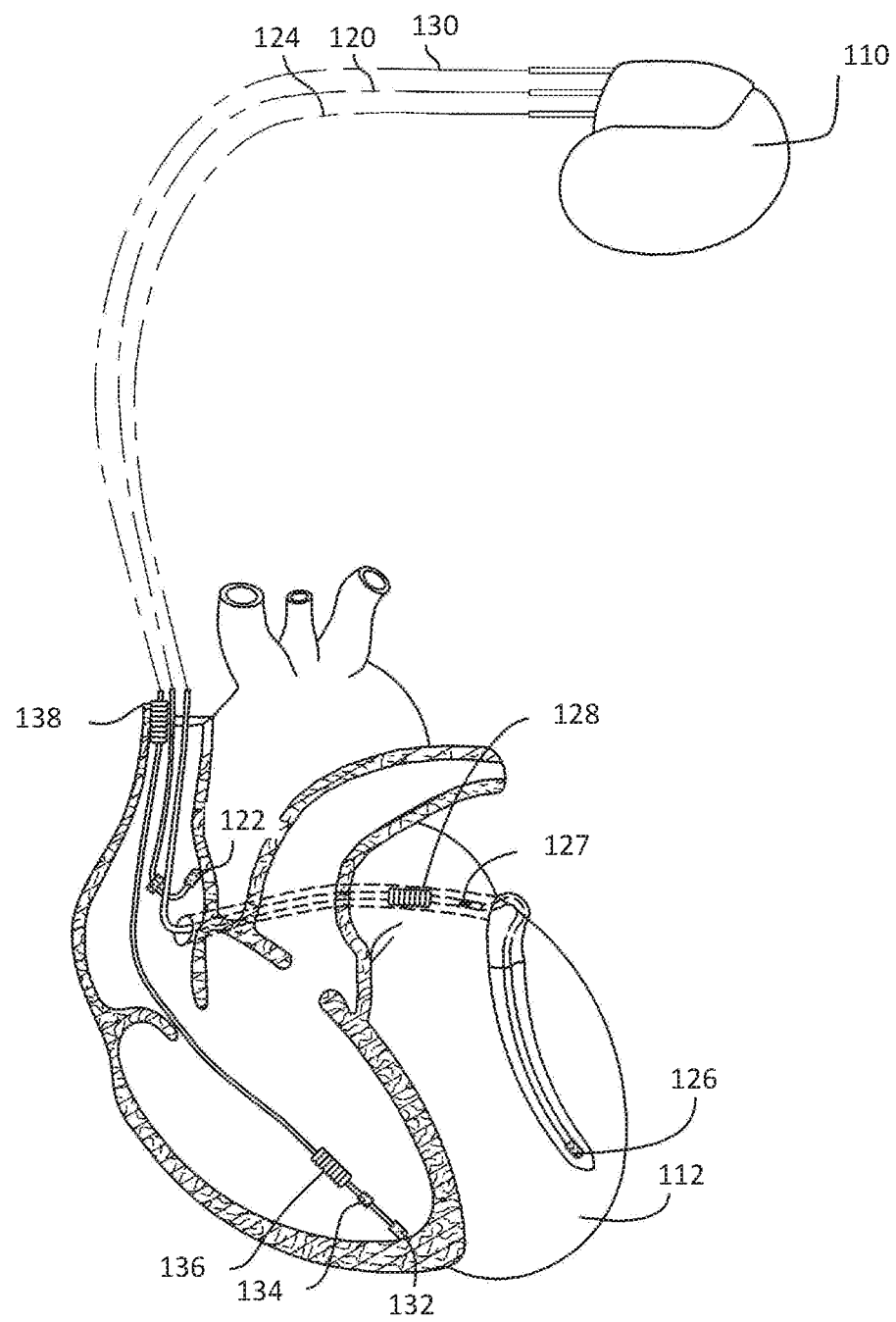
FIG. 1 is a simplified, partly cutaway view illustrating an implantable stimulation device for delivering stimulation and/or shock therapy.

The following description is of the best modes presently contemplated for practicing various embodiments of the present technology. The description is not to be taken in a limiting sense but is made merely for the purpose of describing the general principles of the technology. The scope of the technology should be ascertained with reference to the claims. In the description of the technology that follows, like numerals or reference designators will be used to refer to like parts or elements throughout. In addition, the first digit of a reference number identifies the drawing in which the reference number first appears.

The disclosed embodiments of the present technology generally pertain to IMDs, and methods for use therewith, that detect when an IMD is within or otherwise exposed to an MRI system. Accordingly, an exemplary IMD in which embodiments of the present technology are useful is first described with reference to FIGS. 1 and 2. However, it should be noted that embodiments of the present technology are not limited to use with the exemplary IMD described below.

Exemplary IMD

Referring to FIG. 1, an exemplary IMD 110 (also referred to as a pacing device, a pacing apparatus, a stimulation device, an implantable device or simply a device) is in electrical communication with a patient's heart 112 by way of three leads, 120, 124 and 130, suitable for delivering multi-chamber stimulation. While not necessary to perform embodiments of the present technology, the exemplary IMD 110 is also capable of delivering shock therapy.

To sense atrial cardiac signals and to provide right atrial chamber stimulation therapy, the IMD 110 is coupled to an implantable right atrial lead 120 having at least an atrial tip electrode 122, which typically is implanted in the patient's right atrial appendage. To sense left atrial and ventricular cardiac signals and to provide left-chamber pacing therapy, the IMD 110 is coupled to a "coronary sinus" lead 124 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 124 is designed to receive left atrial and ventricular cardiac signals and to deliver left atrial and ventricular pacing therapy using at least a left ventricular tip electrode 126, left atrial pacing therapy using at least a left atrial ring electrode 127, and shocking therapy using at least a left atrial coil electrode 128. The present technology may of course be practiced with a coronary sinus lead that does not include left atrial sensing, pacing or shocking electrodes.

The IMD 110 is also shown in electrical communication with the patient's heart 112 by way of an implantable right ventricular lead 130 having, in this embodiment, a right ventricular tip electrode 132, a right ventricular ring electrode 134, a right ventricular (RV) coil electrode 136, and an SVC coil electrode 138. Typically, the right ventricular lead 130 is transvenously inserted into the heart 112 so as to place the right ventricular tip electrode 132 in the right ventricular apex so that the RV coil electrode 136 will be positioned in the right ventricle and the SVC coil electrode 138 will be positioned in the superior vena cava. Accordingly, the right ventricular lead 130 is capable of receiving cardiac signals and delivering stimulation in the form of pacing and shock therapy to the right ventricle. It will be understood by those skilled in the art that other lead and electrode configurations such as epicardial leads and electrodes may be used in practicing the technology. For example, only a single lead, or only two leads, may be connected to the IMD. It should also be understood that the IMD can alternatively be a leadless device, such as an implantable monitor and/or a leadless pacer.

Figure 2:
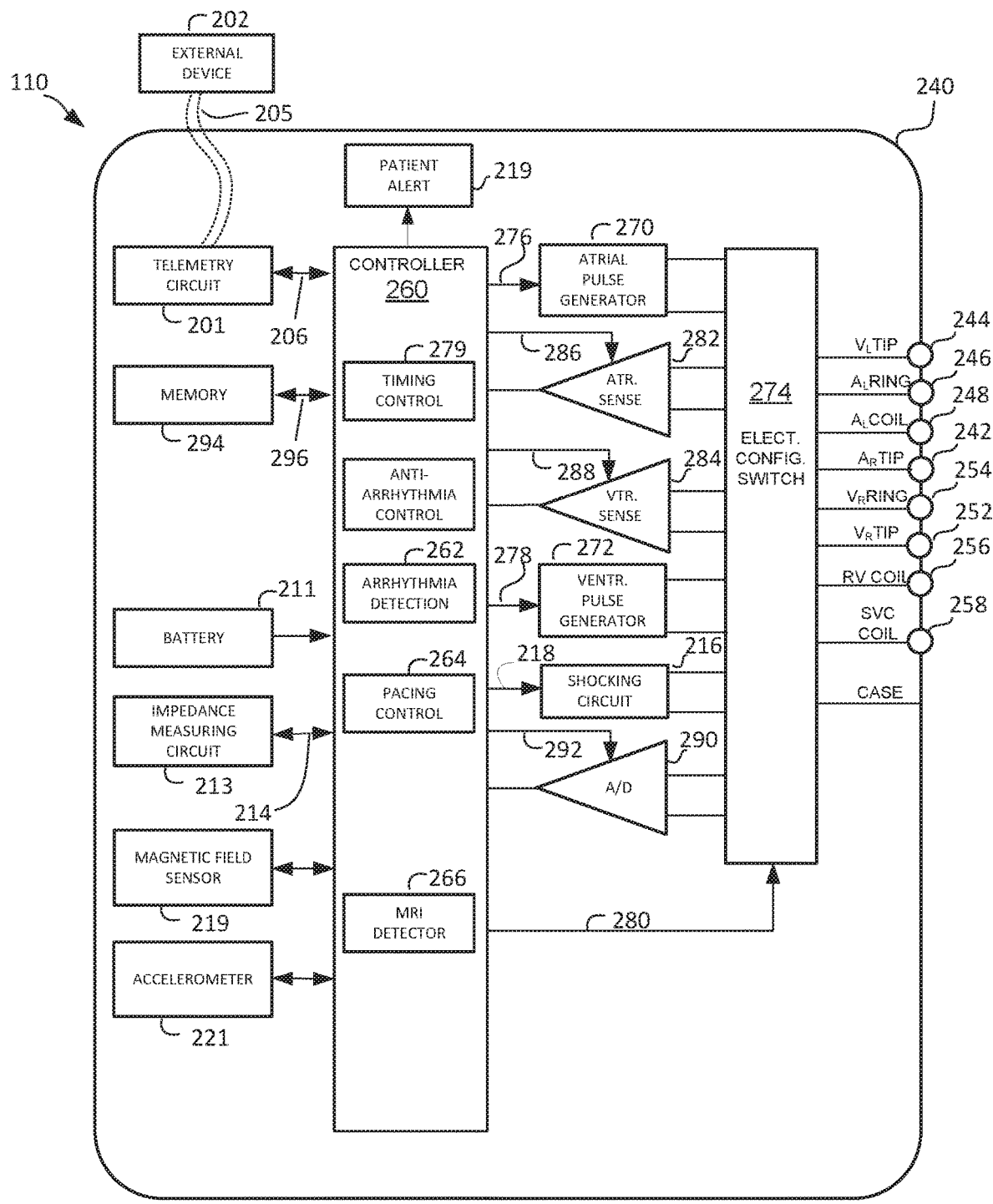
FIG. 2 is a functional block diagram of the implantable stimulation device of FIG. 1, illustrating the basic elements that provide pacing stimulation, cardioversion, and defibrillation in chambers of the heart.

As illustrated in FIG. 2, a simplified block diagram is shown of the multi-chamber implantable device 110, which is capable of treating both fast and slow arrhythmias with stimulation therapy, including pacing, cardioversion and defibrillation stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with pacing, cardioversion and defibrillation stimulation.

The housing 240 for the IMD 110, shown schematically in FIG. 2, is often referred to as the "can", "case" or "case electrode" and may be programmably selected to act as the return electrode for all "unipolar" modes. The housing 240 may further be used as a return electrode alone or in combination with one or more of the coil electrodes, 128, 136 and 138, for shocking purposes. The housing 240 further includes a connector (not shown) having a plurality of terminals, 242, 244, 246, 248, 252, 254, 256, and 258 (shown schematically and, for convenience, the names of the electrodes to which they are connected are shown next to the terminals). As such, to achieve right atrial sensing and pacing, the connector includes at least a right atrial tip terminal ($A_R$ TIP) 242 adapted for connection to the atrial tip electrode 122.

To achieve left atrial and ventricular sensing, pacing and shocking, the connector includes at least a left ventricular tip terminal ($V_L$ TIP) 244, a left atrial ring terminal ($A_L$ RING) 246, and a left atrial shocking terminal ($A_L$ COIL) 148, which are adapted for connection to the left ventricular ring electrode 126, the left atrial tip electrode 127, and the left atrial coil electrode 128, respectively.

To support right ventricle sensing, pacing and shocking, the connector further includes a right ventricular tip terminal ($V_R$ TIP) 252, a right ventricular ring terminal ($V_R$ RING) 254, a right ventricular shocking terminal ($R_V$ COIL) 256, and an SVC shocking terminal (SVC COIL) 258, which are adapted for connection to the right ventricular tip electrode 132, right ventricular ring electrode 134, the RV coil electrode 136, and the SVC coil electrode 138, respectively.

At the core of the IMD 110 is a programmable microcontroller 260 which controls the various types and modes of stimulation therapy. As is well known in the art, the microcontroller 260 typically includes a microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 260 includes the ability to process or monitor input signals (data) as controlled by a program code stored in a designated block of memory. The details of the design of the microcontroller 260 are not critical to the present technology. Rather, any suitable microcontroller 260 can be used to carry out the functions described herein. The use of microprocessor-based control circuits for performing timing and data analysis functions are well known in the art. In specific embodiments of the present technology, the microcontroller 260 performs some or all of the steps associated with arrhythmia detection.

Representative types of control circuitry that may be used with the technology include the microprocessor-based control system of U.S. Pat. No. 4,940,052 (Mann et. al.) and the state-machines of U.S. Pat. No. 4,712,555 (Baker) and U.S. Pat. No. 4,944,298 (Sholder). For a more detailed description of the various timing intervals used within the pacing device and their inter-relationship, see U.S. Pat. No. 4,788,980 (Mann et. al.). The '052, '555, '298 and '980 patents are incorporated herein by reference.

An atrial pulse generator 270 and a ventricular pulse generator 272 generate pacing stimulation pulses for delivery by the right atrial lead 120, the right ventricular lead 130, and/or the coronary sinus lead 124 via an electrode configuration switch 274. It is understood that in order to provide stimulation therapy in each of the four chambers of the heart, the atrial and ventricular pulse generators, 270 and 272, may include dedicated, independent pulse generators, multiplexed pulse generators, or shared pulse generators. The pulse generators, 270 and 272, are controlled by the microcontroller 260 via appropriate control signals, 276 and 278, respectively, to trigger or inhibit the stimulation pulses.

The microcontroller 260 further includes timing control circuitry 279 which is used to control pacing parameters (e.g., the timing of stimulation pulses) as well as to keep track of the timing of refractory periods, noise detection windows, evoked response windows, alert intervals, marker channel timing, etc., which is well known in the art. Examples of pacing parameters include, but are not limited to, atrio-ventricular delay, interventricular delay and interatrial delay.

The switch bank 274 includes a plurality of switches for connecting the desired electrodes to the appropriate I/O circuits, thereby providing complete electrode programmability. Accordingly, the switch 274, in response to a control signal 280 from the microcontroller 260, determines the polarity of the stimulation pulses (e.g., unipolar, bipolar, etc.) by selectively closing the appropriate combination of switches (not shown) as is known in the art.

Atrial sensing circuits 282 and ventricular sensing circuits 284 may also be selectively coupled to the right atrial lead 120, coronary sinus lead 124, and the right ventricular lead 130, through the switch 274 for detecting the presence of cardiac activity in each of the four chambers of the heart. Accordingly, the atrial (ATR. SENSE) and ventricular (VTR. SENSE) sensing circuits, 282 and 284, may include dedicated sense amplifiers, multiplexed amplifiers, or shared amplifiers. The switch 274 determines the "sensing polarity" of the cardiac signal by selectively closing the appropriate switches, as is also known in the art. In this way, the clinician may program the sensing polarity independent of the stimulation polarity.

Each sensing circuit, 282 and 284, preferably employs one or more low power, precision amplifiers with programmable gain and/or automatic gain control, bandpass filtering, and a threshold detection circuit, as known in the art, to selectively sense the cardiac signal of interest. The automatic gain control enables the IMD 110 to deal effectively with the difficult problem of sensing the low amplitude signal characteristics of atrial or ventricular fibrillation. Such sensing circuits, 282 and 284, can be used to determine cardiac performance values used in the present technology. Alternatively, an automatic sensitivity control circuit may be used to effectively deal with signals of varying amplitude.

The outputs of the atrial and ventricular sensing circuits, 282 and 284, are connected to the microcontroller 260 which, in turn, are able to trigger or inhibit the atrial and ventricular pulse generators, 270 and 272, respectively, in a demand fashion in response to the absence or presence of cardiac activity, in the appropriate chambers of the heart. The sensing circuits, 282 and 284, in turn, receive control signals over signal lines, 286 and 288, from the microcontroller 260 for purposes of measuring cardiac performance at appropriate times, and for controlling the gain, threshold, polarization charge removal circuitry (not shown), and timing of any blocking circuitry (not shown) coupled to the inputs of the sensing circuits, 282 and 286. The sensing circuits can be used, for example, to acquire IEGM signals.

For arrhythmia detection, the IMD 110 includes an arrhythmia detector 262 that utilizes the atrial and ventricular sensing circuits, 282 and 284, to sense cardiac signals to determine whether a rhythm is physiologic or pathologic. The timing intervals between sensed events (e.g., P-waves, R-waves, and depolarization signals associated with fibrillation) are then classified by the microcontroller 260 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to assist with determining the type of remedial therapy that is needed (e.g., bradycardia pacing, anti-tachycardia pacing, cardioversion shocks or defibrillation shocks, collectively referred to as "tiered therapy"). The arrhythmia detector 262 can be implemented within the microcontroller 260, as shown in FIG. 2. Thus, this detector 262 can be implemented by software, firmware, or combinations thereof. It is also possible that all, or portions, of the arrhythmia detector 262 can be implemented using hardware. Further, it is also possible that all, or portions, of the arrhythmia detector 262 can be implemented separate from the microcontroller 260.

The stimulation device 110 is also shown as including a pacing controller 264, which can adjust a pacing rate and/or pacing intervals. The pacing controller 264 can be implemented within the microcontroller 260, as shown in FIG. 2. Thus, the pacing controller 264 can be implemented by software, firmware, or combinations thereof. It is also possible that all, or portions, of the pacing controller 264 can be implemented using hardware.

The IMD 110 is also shown as including a magnetic field sensor 219 and an accelerometer 221. The magnetic field sensor 219 of the IMD 110 can be or include, e.g., one or more Hall effect sensor, one or more giant magnetoresistance (MGR.) sensor, and/or one or more reed switch, but is not limited thereto.

An exemplary GMR sensor is described in U.S. Pat. No. 6,101,417 (Vogel), which is incorporated herein by reference. For another example, commercially available GMR sensors are manufactured and sold by NVE Corporation (headquartered in Eden Prairie, Minn.). Exemplary GMR sensors produced by NVE Corporation include the BA010-01, BA020 and BD027-14E sensors.

Depending upon implementation, the magnetic field sensor 219 of the IMD 110 can measure a magnetic field along one-axis, two-axes, or three-axis. Where the magnetic field sensor 219 can measure the magnetic field along one-axis, it can be referred to as a single-axis magnetic field sensor, or as a one-dimensional (1D) magnetic field sensor. Where the magnetic field sensor 219 can measure the magnetic field along two-axes that are orthogonal to one another, it can be referred to as a two-axis magnetic field sensor, or as a two-dimensional (2D) magnetic field sensor. Where the magnetic field sensor 219 can measure the magnetic field along three-axes that are orthogonal to one another, it can be referred to as a three-axis magnetic field sensor, or as a three-dimensional (3D) magnetic field sensor.

A two-axis magnetic field sensor or a three-axis magnetic field sensor can also be referred to as a multi-axis magnetic field sensor or a multi-dimensional magnetic field sensor. Where the magnetic field sensor 219 is a multi-axis magnetic field sensor it can include two or three sensors aligned along orthogonal axes, wherein, for example, each of the two or three sensors can be a Hall effect sensor, GMR sensor, or reed switch, but is not limited thereto. The three potential axes along which a magnetic field sensor 219 can detect a magnetic field include the z-axis, the x-axis and the y-axis, which are orthogonal to one another. For the purpose of the discussion, an axis that is parallel to the ground and parallel to a longitudinal axis of the bore of an MRI system will be referred to as the z-axis; an axis that is parallel to the ground and perpendicular to the longitudinal axis of the bore of an MRI system (and thus perpendicular to the z-axis) will be referred to as the x-axis; and an axis that is perpendicular to the ground and perpendicular to the longitudinal axis of the bore of an MRI system (and thus perpendicular to the z-axis) will be referred to as the y-axis; wherein the z-axis, the x-axis, and the y-axis are orthogonal (i.e., perpendicular) to one another.

Where the magnetic field sensor 219 measures magnetic fields along more than one axis, it can include multiple single-axis sensors arranged to detect magnetic fields along multiple axes that are orthogonal to one another. For example, a magnetic field sensor that detects magnetic fields along two different axis can include a two-axis Hall effect sensor, or two one-axis Hall effect sensors that are arranged orthogonal to one another. For another example, a magnetic field sensor that detects magnetic fields along three different axis can include a three-axis Hall effect sensor, or three one-axis Hall effect sensors that are arranged orthogonal to one another. For another example, a magnetic field sensor that detects magnetic fields along three different axis can include three reed switches arranged orthogonal to one another.

It is also possible that the magnetic field sensor 219 (e.g., including one or more GMR sensor, reed switch or Hall effect sensor) may also be used by a clinician to perform various test functions of the IMD 110 and/or to signal the microcontroller 260 that the external programmer 202 is in place to receive or transmit data to the microcontroller 260 through the telemetry circuits 201.

Signals produced and output by the magnetic field sensor 219 may be analyzed with respect to frequency content, energy, duration, amplitude and/or other characteristics. Such signals may or may not be amplified and/or filtered prior to being analyzed. For example, filtering may be performed using lowpass, highpass and/or bandpass filters. The signals output by the magnetic field sensor 219 can be analog signals, which can be analyzed in the analog domain, or can be converted to digital signals (by an analog-to-digital converter, e.g., 290) and analyzed in the digital domain. Alternatively, the signals output by the magnetic field sensor 219 can already be in the digital domain. The signals output by the magnetic field sensor 219 can be analyzed by the microcontroller 260 and/or other circuitry. In certain embodiments, the magnetic field sensor 219 is packaged along with an integrated circuit (IC) that is designed to analyze the signals output by the magnetic field sensor 219. In such embodiments, the output(s) of the packaged sensor/IC can be an indication of the magnitude of the magnetic field(s) measured along one or more axes. The output(s) of the magnetic field sensor 219 can be compared, e.g., by one or more comparators, to one or more magnetic field threshold(s). Alternatively, the magnetic field sensor 219 can have one or more input(s) that accept one or more analog or digital threshold(s), and the magnetic field sensor 219 can produce one or more output(s) that indicate whether or not such threshold(s) are exceeded. In certain embodiments, the magnetic field sensor 219 can be packaged along with an IC that performs signal conditioning (e.g., amplification and/or filtering), performs analog-to-digital conversions, and stores digital data (indicative of the sensor output(s)) in memory (e.g., RAM, which may or may not be within the same package). In such embodiments, the microcontroller 260 or other circuitry can read the digital data from the memory and analyze the digital data. Other variations are also possible, and within the scope of the present technology. Additional details of how to analyze signals output by the magnetic field sensor 219 are discussed below.

The accelerometer 221 of the IMD 110 can be or include, e.g., a MEMS (micro-electromechanical system) multi-axis accelerometer of the type exploiting capacitive or optical cantilever beam techniques, or a piezoelectric accelerometer that employs the piezoelectric effect of certain materials to measure dynamic changes in mechanical variables (e.g., acceleration, and/or vibration), but is not limited thereto. As will be described in additional detail below, depending upon implementation, the accelerometer 221 can be used to detect posture and/or motion of a patient in which an IMD 110 including the accelerometer 221 is implanted.

Where the accelerometer 221 is a multi-axis accelerometer it can include two or three sensors aligned along orthogonal axes. Exemplary multi-axis accelerometers (also referred to as multi-dimensional accelerometers) that can be used are described U.S. Pat. No. 6,658,292 (Kroll et al.) and U.S. Pat. No. 6,466,821 (Pianca et al.), each of which is incorporated herein by reference. For another example, a commercially available micro-electromechanical system (MEMS) accelerometer marketed as the ADXL345 by Analog Devices, Inc. (headquartered in Norwood, Mass.) is a three-axis accelerometer and includes polysilicon springs that provide a resistance against acceleration forces. The term MEMS has been defined generally as a system or device having micro-circuitry on a tiny silicon chip into which some mechanical device such as a mirror or a sensor has been manufactured. The aforementioned ADXL345 includes a micro-machined accelerometer co-packaged with a signal processing IC.

Another commercially available MEMS accelerometer is the ADXL327 by Analog Devices, Inc., which is a small, thin, low power, complete three axis accelerometer with signal conditioned voltage outputs. In the ADXL327, the mechanical sensor and signal conditioning IC are packaged together. A further commercially available MEMS accelerometer that can be used is the LIS3DH three-axis accelerometer by STMicroelectronics (headquartered in Geneva, Switzerland).

Additional and/or alternative types of accelerometers may also be used. For example, it is also within the scope of the present technology for the sensor 219 to be a beam-type of accelerometer, an example of which is described in U.S. Pat. No. 6,252,335 (Nilsson et al.), which is incorporated herein by reference.

In certain embodiments, the accelerometer 221 is implemented using one or more strain gauges. For example, a conventional type of strain gauge is formed of a thin film with a conductive wire or wires and associated terminals where tension causes an increase in resistance at the terminals and where compression decreases resistance at the terminals (e.g., a piezoresistive gauge). Vibrations and/or acoustics may cause such a film to cycle between tension and compression and hence produce an oscillating signal as resistance changes. The oscillating signal may be analyzed to determine the frequency of oscillation and/or the morphology of the signal. A strain gauge may be configured to sense strain along a particular direction. Multiple strain gauges may be included in the accelerometer 221 to sense strain along different directions.

The accelerometer 221 may be included within the case 240 of the IMD 110. Alternatively, the accelerometer 221 can be included in or be otherwise be attached to a lead (e.g., 120, 124 or 130), in which case the accelerometer 221 can communicate with the IMD 110 via the lead or through electrical signals conducted by body tissue and/or fluid. For example, an exemplary lead can include the accelerometer 221 proximate to one end and a connector at the other end that allows for connection to an implantable device such as the IMD 110.

Signals produced and output by the accelerometer 221 may be analyzed with respect to frequency content, energy, duration, amplitude and/or other characteristics. Such signals may or may not be amplified and/or filtered prior to being analyzed. For example, filtering may be performed using lowpass, highpass and/or bandpass filters. The signals output by the accelerometer 221 can be analog signals, which can be analyzed in the analog domain, or can be converted to digital signals (by an analog-to-digital converter, e.g., 290) and analyzed in the digital domain. Alternatively, the signals output by the accelerometer 221 can already be in the digital domain. The signals output by the accelerometer 221 can be analyzed by the microcontroller 260 and/or other circuitry. In certain embodiments, the accelerometer 221 is packaged along with an integrated circuit (IC) that is designed to analyze the signals output by the accelerometer 221. In such embodiments, an output of the packaged sensor/IC can be an indication of position or posture, and/or an indication of motion. In other embodiments, the accelerometer 221 can be packaged along with an IC that performs signal conditioning (e.g., amplification and/or filtering), performs analog-to-digital conversions, and stores digital data (indicative of the sensor output) in memory (e.g., RAM, which may or may not be within the same package). In such embodiments, the microcontroller 260 or other circuitry can read the digital data from the memory and analyze the digital data. Other variations are also possible, and within the scope of the present technology.

Additional details of how to analyze signals output by the accelerometer 221 are discussed below.

Additionally, the IMD 110 is shown as including an MRI detector 266, which can detect when the IMD 110 is likely within or otherwise being exposed to a magnetic field from an MRI system. As will be described in additional detail below, with reference to the flow diagrams of FIGS. 3 through 6, the MRI detector 266 can use the magnetic field sensor 219 and/or the accelerometer 221 to detect when the IMD is likely within or otherwise being exposed to a magnetic field from an MRI system, and in response thereto, can cause the IMD 110 to mode switch from a normal operation mode to an MRI safe mode. The MRI detector 266 can also use the magnetic field sensor 219 and/or the accelerometer 221 to detect when the IMD is likely no longer within or otherwise being exposed to a magnetic field from an MRI system, and in response thereto, can cause the IMD 110 to mode switch from the MRI safe mode back to the normal operation mode of the IMD 110. Additional details of the operation of the MRI detector 266, according to various embodiments of the present technology, are discussed below. The MRI detector 266 can be implemented within the microcontroller 260, as shown in FIG. 2. Thus, the MRI detector 266 can be implemented by software, firmware, hardware, or combinations thereof. It is also possible that all, or portions, of the MRI detector 266 can be implemented using dedicated hardware, such as using an application specific integrated circuit (ASIC). More generally, the MRI detector 266 can be implemented by a controller, wherein the controller may be a microcontroller (e.g., 260), or an ASIC, but is not limited thereto.

Still referring to FIG. 2, cardiac signals and/or other signals can be applied to the inputs of an analog-to-digital (A/D) data acquisition system 290. The data acquisition system 290 is configured to acquire intracardiac electrogram signals, convert the raw analog data into a digital signal, and store the digital signals for later processing and/or telemetric transmission to an external device 202. The data acquisition system 290 is coupled to the right atrial lead 120, the coronary sinus lead 124, and the right ventricular lead 130 through the switch 274 to sample cardiac signals across any pair of desired electrodes.

The data acquisition system 290 can be coupled to the microcontroller 260, or other detection circuitry, for detecting an evoked response from the heart 112 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 260 detects a depolarization signal during a window following a stimulation pulse, the presence of which indicates that capture has occurred. The microcontroller 260 enables capture detection by triggering the ventricular pulse generator 272 to generate a stimulation pulse, starting a capture detection window using the timing control circuitry 279 within the microcontroller 260, and enabling the data acquisition system 290 via control signal 292 to sample the cardiac signal that falls in the capture detection window and, based on the amplitude, determines if capture has occurred. The data acquisition system 290 may also be used to acquire signals produced by the sensors 219 and/or 221, and may convert analog signals produced by such sensor to digital signals. It is also possible that the sensors 219 and/or 221 output digital signals.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Kleks et. al.), which patents are hereby incorporated herein by reference. The type of capture detection system used is not critical to the present technology.

The microcontroller 260 is further coupled to the memory 294 by a suitable data/address bus 296, wherein the programmable operating parameters used by the microcontroller 260 are stored and modified, as required, in order to customize the operation of the IMD 110 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 112 within each respective tier of therapy. The memory 294 can also be used to store data relating to one or more magnetic field thresholds, and other information that can be utilized in embodiments of the present technology described herein.

The operating parameters of the IMD 110 may be non-invasively programmed into the memory 294 through a telemetry circuit 201 in telemetric communication with an external device 202, such as a programmer, transtelephonic transceiver, or a diagnostic system analyzer. The telemetry circuit 201 can be activated by the microcontroller 260 by a control signal 206. The telemetry circuit 201 advantageously allows intracardiac electrograms and status information relating to the operation of the device 110 (as contained in the microcontroller 260 or memory 294) to be sent to the external device 202 through an established communication link 204. The telemetry circuit 201 can also be used to trigger alarms or alerts of the external device 202, or to instruct the external device 202 to notify a caregiver regarding detection of various episodes, occurrences and changes in conditions that are detected using embodiments of the present technology.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734 entitled "Efficient Generation of Sensing Signals in an Implantable Medical Device such as a Pacemaker or ICD" (McClure et al.), which patents are hereby incorporated herein by reference.

The IMD 110 additionally includes a battery 211 which provides operating power to all of the circuits shown in FIG. 2. If the implantable device 110 also employs shocking therapy, the battery 211 should be capable of operating at low current drains for long periods of time, and then be capable of providing high-current pulses (for capacitor charging) when the patient requires a shock pulse. The battery 211 should also have a predictable discharge characteristic so that elective replacement time can be detected.

As further shown in FIG. 2, the IMD 110 is also shown as having an impedance measuring circuit 213 which is enabled by the microcontroller 260 via a control signal 214. The known uses for an impedance measuring circuit 213 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds and heart failure condition; detecting when the device has been implanted; measuring stroke volume; and detecting the opening of heart valves, etc. The impedance measuring circuit 213 is advantageously coupled to the switch 274 so that any desired electrode may be used. The impedance measuring circuit 213 is not critical to the present technology and is shown only for completeness.

In the case where the IMD 110 is also intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 260 further controls a shocking circuit 216 by way of a control signal 218. The shocking circuit 216 generates shocking pulses of low (up to 0.5 Joules), moderate (0.5-10 Joules), or high energy (11 to 40 Joules), as controlled by the microcontroller 260. Such shocking pulses are applied to the patient's heart 112 through at least two shocking electrodes, and as shown in this embodiment, selected from the left atrial coil electrode 228, the RV coil electrode 236, and/or the SVC coil electrode 238. As noted above, the housing 240 may act as an active electrode in combination with the RV electrode 236, or as part of a split electrical vector using the SVC coil electrode 238 or the left atrial coil electrode 228 (i.e., using the RV electrode as a common electrode).

The above described IMD 110 was described as an exemplary pacing device. One or ordinary skill in the art would understand that embodiments of the present technology can be used with alternative types of implantable devices. Accordingly, embodiments of the present technology should not be limited to use only with the above described device.

Embodiments of the Present Technology

As mentioned above, in order to avoid under- or over-sensing the cardiac signals when the IMD 110 is in the presence of relatively large external magnetic fields produced by an MRI system, the IMD 110 may switch modes of operation from a normal mode to an MRI safe mode when the IMD 110 enters or is otherwise exposed to the magnetic field. While in the MRI safe mode, the IMD 110 may change the algorithms, software, and/or logical steps by which cardiac signals are monitored, and/or by which pacing and/or other cardiac therapy is delivered. For example, the IMD 110 may change which algorithms are used to identify an arrhythmia. Alternatively, the IMD 110 may cease measuring or sensing cardiac signals. Once the IMD 110 leaves or is otherwise not exposed to the strong magnetic field from an MRI system, the IMD 110 may switch back to its normal mode of operation, which is also referred to as the normal operational mode. In the normal operational mode, the IMD 110 may resume monitoring cardiac signals as the IMD 110 did before the IMD 110 was exposed to a strong magnetic field from an MRI system. Exemplary normal operational modes and MRI safe modes are discussed below.

Figure 3:
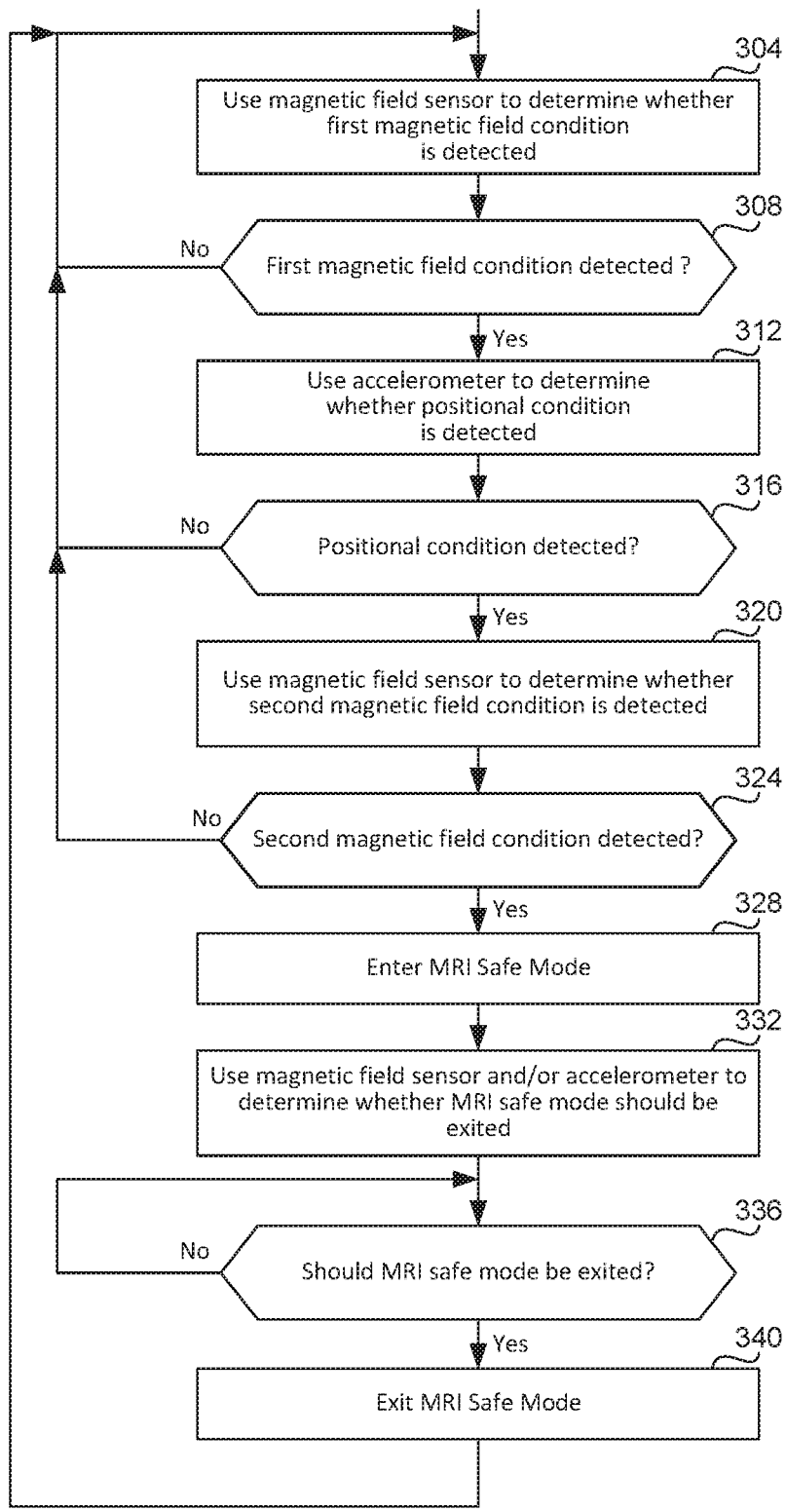
FIG. 3 is a high level flow diagram that is used to summarize methods according to certain embodiments of the present technology.

FIG. 3 will now be used to summarize methods, according to certain embodiments of the present technology, which can be used to detect, with increased specificity, when an IMD (e.g., 110) is within or otherwise exposed to an MRI system, and thus, should be automatically switched to an MRI safe mode. Such methods are for use with an IMD (e.g., 110) that includes a magnetic field sensor (e.g., 219) and an accelerometer (e.g., 221) and is capable of automatically mode switching to an MRI safe mode. More specifically, such methods can be used by the IMD to automatically mode switch to an MRI safe mode when appropriate, and to automatically exit the MRI safe mode when appropriate, with increased specificity. Exemplary types and details of the magnetic field sensor (e.g., 219) were described above in the discussion of FIG. 2. Additionally, exemplary types and details of the accelerometer (e.g., 221) were described above in the discussion of FIG. 2.

Referring to FIG. 3, step 304 involves using the magnetic field sensor to determine whether a first magnetic field condition is detected. As indicated by the decision block 308, if the first magnetic field condition is not detected then flow returns to step 304, and if the first magnetic field condition is detected then flow goes to step 312. Additional details of steps 304 and 308, according to certain embodiments of the present technology, are described below with reference to FIGS. 4 though 6.

Still referring to FIG. 3, step 312 involves using the accelerometer to determine whether a positional condition is detected. As indicated by the decision block 316, if the positional condition is not detected then flow returns to step 304, and if the positional condition is detected then flow goes to step 320.

In accordance with certain embodiments, the positional condition is the patient being in a supine position. In accordance with other embodiments, the positional condition is the patient both being in a supine position and being stationary. In still other embodiments, the positional condition is the patient being stationary. In other words, in certain embodiments the accelerometer is used at step 312 to determine whether a patient is in a supine position (which is the position the patient will be when lying down in an MRI system, which can also be referred to as an MRI scanner), and/or can also be used at step 312 to determine whether the patient is stationary (which is how the patient will be instructed to be when lying down in an MRI system). An accelerometer (e.g., 221) can be used to detect whether a patient is stationary by measuring motion along one or more axes and comparing the measured motion to one or more respective motion threshold(s). In other words, the term stationary, as used herein, refers to detected motion being below one or more motion threshold(s). The motion threshold(s) can, for example, be set by default, or can be calibrated for the specific patient.

Still referring to FIG. 3, step 320 involves using the magnetic field sensor to determine whether a second magnetic field condition is detected, wherein the second magnetic field condition differs from the first magnetic field condition. As indicated by the decision block 324, if the second magnetic field condition is not detected then flow returns to step 304, and if the second magnetic field condition is detected then flow goes to step 328. Additional details of steps 320 and 324, according to certain embodiments of the present technology, are described below with reference to FIGS. 4 though 6.

Step 328 involves performing a mode switch to the MRI safe mode. As can be appreciated from the above discussion, such a mode switch to the MRI safe mode is based at least in part on the the IMD determining that the first and second magnetic field conditions and the positional condition are detected, and thus, that there is high probability that the patient is actually within an MRI system. The MRI safe mode to which the IMD is switched at step 328 can depend on the normal operational mode of the IMD. For example, if the normal operational mode of the IMD is a Dxx mode (e.g., a DDDR, DDD, DDI, or DVI mode), then the mode switch to the MRI safe mode at step 328 can be a mode switch to DOO (i.e., the MRI safe mode can be a DOO mode). For another example, if the normal operational mode of the IMD is a Vxx mode (e.g., a VDDR, VDD, VDI, or VI mode), then the mode switch to the MRI safe mode at step 328 can be a mode switch to VOO or pacer off (i.e., the MRI safe mode can be a VOO mode or pacer off (no pacing)). For still another embodiment, if the normal operational mode of the IMD is an Axx mode (e.g., an ADDR, ADD, ADI, or AVI mode), then the mode switch to the MRI safe mode at step 328 can be a mode switch to AOO (i.e., the MRI safe mode can be a AOO mode). These are just a few examples, which are not meant to be all encompassing.

Still referring to FIG. 3, step 332 involves using the magnetic field sensor (e.g., 221) and/or the accelerometer (e.g., 219) of the IMD to determine whether the MRI safe mode should be exited. As indicated by the decision block 336, where the MRI safe mode should not be exited flow returns to step 332, and if the MRI safe mode should be exited then flow goes to step 340. At step 340, the MRI safe mode is exited and the IMD returns to its normal operational mode. Preferably, the MRI safe mode should be exited as soon as possible after the patient is no longer within or otherwise exposed to the MRI system, in order to minimize the probability of the IMD failing to detect and appropriately treat a tachycardia or fibrillation, and/or in order to maximize the probability that the patient is optimally paced.

Additional details of the methods summarized in FIG. 3 will now be described below with reference to FIGS. 4 though 6. More specifically, FIG. 4 will first be used to describe embodiments that can be used where the magnetic field sensor of the IMD is a single-axis magnetic field. Preferably, where an IMD includes a single-axis magnetic field sensor, the single-axis along which magnetic field sensor measures a magnetic field is the z-axis, i.e., the axis that is parallel to the ground and parallel to the longitudinal axis of the bore of an MRI system, when a patient is lying therein.

Figure 4:
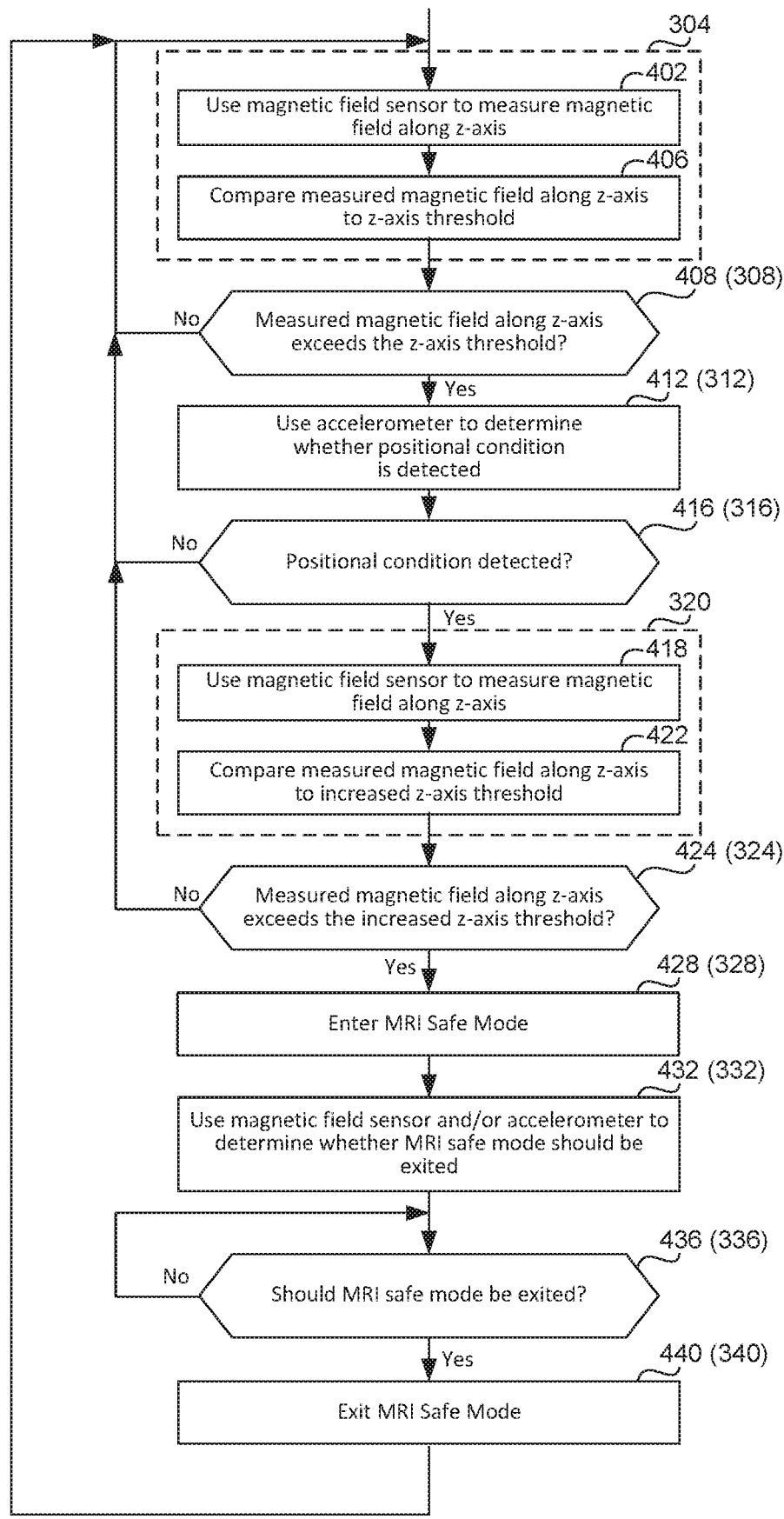
FIG. 4 is a high level flow diagram that is used to provide additional details of the methods introduced with reference to FIG. 3, according to specific embodiments of the present technology.

Referring to FIG. 4, step 402 involves using the magnetic field sensor to measure a magnetic field along the z-axis, step 404 involves comparing the measured magnetic field along the z-axis to a z-axis magnetic field threshold, and step 406 involves determining whether the measured magnetic field along the z-axis exceeds the z-axis magnetic field threshold. As can be appreciated by the dashed-block labeled 304, steps 402 and 404 shown therein are a specific implementation of step 304 in FIG. 3. Additionally, step 406 is a specific implementation of step 308 in FIG. 3.

Steps 412 and 416 in FIG. 4 are the same as steps 312 and 316 in FIG. 3, and thus, need not be described in great detail again. In accordance with certain embodiments, the positional condition being monitored for at these steps is the patient being in a supine position. In accordance with other embodiments, the positional condition is the patient both being in a supine position and being stationary. In still other embodiments, the positional condition is the patient being stationary. In other words, in certain embodiments the accelerometer is used at step 412 to determine whether a patient is in a supine position (which is the position the patient will be when lying down in an MRI system, which can also be referred to as an MRI scanner), and/or the accelerometer can also be used at step 412 to determine whether the patient is stationary (which is how the patient will be instructed to be when lying down in an MRI system).

Still referring to FIG. 4, step 418 involves using the magnetic field sensor to measure the magnetic field along the z-axis, and step 422 involves comparing the measured magnetic field along the z-axis to an increased z-axis magnetic field threshold, and step 424 involves determining whether the measured magnetic field along the z-axis exceeds the increased z-axis magnetic field threshold. If the value of the magnetic field measured along the z-axis at step 402 was saved (e.g., in memory or a register), then step 418 can be skipped and the saved value (determined at step 402) can be used to perform the comparison at step 422. However, if steps 402 and 406 are performed substantially simultaneously and simply produce a binary answer, then the magnetic field along the z-axis will need to be measured again at step 418.

As can be appreciated by the dashed-block labeled 320, steps 418 and 422 shown therein are a specific implementation of step 320 in FIG. 3. Additionally, step 424 is a specific implementation of step 324 in FIG. 3. The magnetic field thresholds are preferably specified in the same unit of measure that is output by the magnetic field sensor, which unit of measurement can be Magnetic Flux Density (B) or Magnetic Field Strength (H), but is not limited thereto. It would also be possible to convert a measured unit of measurement to the same unit of measurement as the thresholds, if they were not expressed in the same units. The increased z-axis magnetic field threshold (used at step 424) can be, e.g., a margin or percentage greater than the z-axis magnetic field threshold (used at step 406).

If the answer to the determination at step 424 is yes (i.e., if the measured magnetic field along the z-axis exceeds the increased z-axis magnetic field threshold) then flow goes to step 428. If the answer to the determination at step 424 is no (i.e., if the measured magnetic field along the z-axis does not exceed the increased z-axis magnetic field threshold) then flow goes back to step 404. Steps 428, 432, 436, and 440 are the same, respectively, as steps 328, 332, 336 and 340 described above with reference to FIG. 3, and thus, need not be described again.

Figure 5:
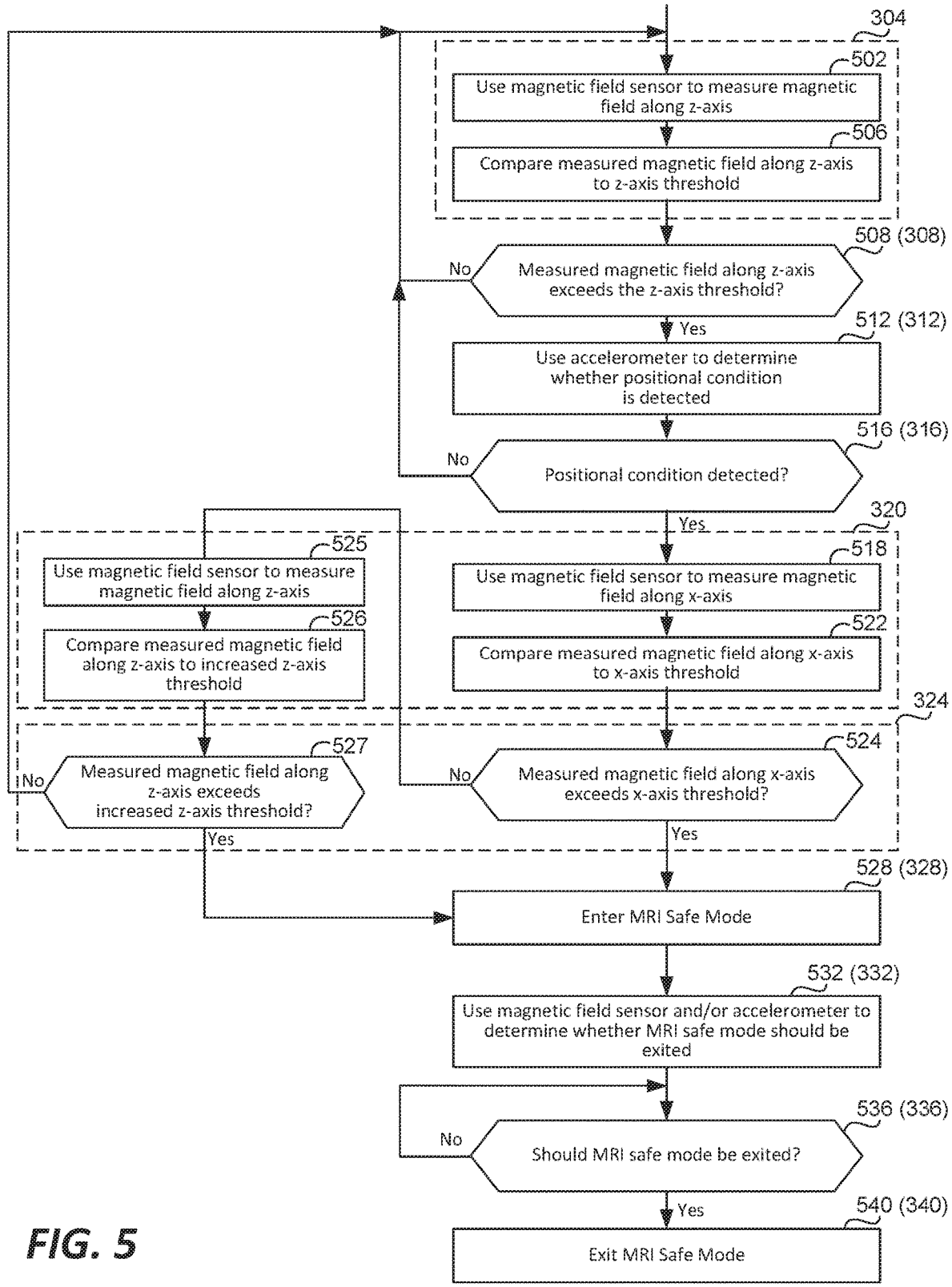
FIG. 5 is a high level flow diagram that is used to provide additional details of the methods introduced with reference to FIG. 3, according to other embodiments of the present technology.

FIG. 5 will now be used to describe embodiments that can be used where the magnetic field sensor of the IMD is a two-axis magnetic field sensor, which as noted above, can also be referred to as a 2D magnetic field sensor. Preferably, where an IMD includes a two-axis magnetic field sensor, the two-axis magnetic field sensor measures the magnetic field along the z-axis (i.e., the axis that is parallel to the ground and parallel to the longitudinal axis of the bore of an MRI system) and along either the x-axis or the y-axis. For the purpose of this discussion, it will be assumed that the two-axis magnetic field sensor measures the magnetic field along the z-axis and the x-axis.

Referring to FIG. 5, step 502 involves using the magnetic field sensor to measure a magnetic field along the z-axis, step 506 involves comparing the measured magnetic field along the z-axis to a z-axis magnetic field threshold, and step 508 involves determining whether the measured magnetic field along the z-axis exceeds the z-axis magnetic field threshold. As can be appreciated by the dashed-block labeled 304, steps 502 and 506 shown therein are a specific implementation of step 304 in FIG. 3. Additionally, step 508 is a specific implementation of step 308 in FIG. 3. Further, as can be appreciated by comparing FIG. 5 to FIG. 4, steps 502, 504, 506 and 508 in FIG. 5 are the same, respectively, as steps 402, 404, 406 and 408 in FIG. 4.

Steps 512 and 516 in FIG. 5 are the same as steps 312 and 316 in FIG. 3, and thus, need not be described in great detail again. In accordance with certain embodiments, the positional condition is being monitored for at these steps the patient being in a supine position. In accordance with other embodiments, the positional condition is the patient both being in a supine position and being stationary. In still other embodiments, the positional condition is the patient being stationary. In other words, in certain embodiments the accelerometer is used at step 512 to determine whether a patient is in a supine position (which is the position the patient will be when lying down in an MRI system, which can also be referred to as an MRI scanner), and/or the accelerometer can also be used at step 512 to determine whether the patient is stationary (which is how the patient will be instructed to be when lying down in an MRI system).

Still referring to FIG. 5, step 518 involves using the magnetic field sensor to measure the magnetic field along the x-axis, and step 522 involves comparing the measured magnetic field along the x-axis to an x-axis magnetic field threshold, and step 524 involves determining whether the measured magnetic field along the x-axis exceeds the x-axis magnetic field threshold. If the answer to the determination at step 524 is yes (i.e., if the measured magnetic field along the x-axis exceeds the x-axis magnetic field threshold) then flow goes to step 528. Steps 528, 532, 536, and 540 are the same, respectively, as steps 328, 332, 336 and 340 described above with reference to FIG. 3, and thus, need not be described again. If the answer to the determination at step 524 is no (i.e., if the measured magnetic field along the x-axis does not exceed the x-axis magnetic field threshold) then flow goes to step 525.

Step 525 involves using the magnetic field sensor to measure the magnetic field along the z-axis, and step 526 involves comparing the measured magnetic field along the z-axis to an increased z-axis magnetic field threshold, and step 527 involves determining whether the measured magnetic field along the z-axis exceeds the increased z-axis magnetic field threshold. If the value of the magnetic field measured along the z-axis at step 502 was saved (e.g., in memory or a register), then step 525 can be skipped and the saved value (determined at step 502) can be used to perform the comparison at step 526. However, if steps 502 and 506 are performed substantially simultaneously and simply produce a binary answer, then the magnetic field along the z-axis will need to be measured again at step 525.

If the answer to the determination at step 527 is yes (i.e., if the measured magnetic field along the z-axis exceeds the increased z-axis magnetic field threshold) then flow goes to step 528. If the answer to the determination at step 527 is no (i.e., if the measured magnetic field along the z-axis does not exceed the increased z-axis magnetic field threshold) then flow goes back to step 504. Steps 528, 532, 536, and 540 are the same, respectively, as steps 328, 332, 336 and 340 described above with reference to FIG. 3, and thus, need not be described again.

As can be appreciated by the dashed-block labeled 320, steps 518, 522, 525 and 526 shown therein are a specific implementation of step 320 in FIG. 3. Additionally, step 524 and 527 are a specific implementation of step 324 in FIG. 3. In the embodiments described with reference to FIG. 5, an MRI safe mode may be entered when measured magnetic fields along two axes both exceed respective first thresholds, or when the measured magnetic field along a single axis exceeds an increased threshold (which is greater than its respective first threshold).

Figure 6:
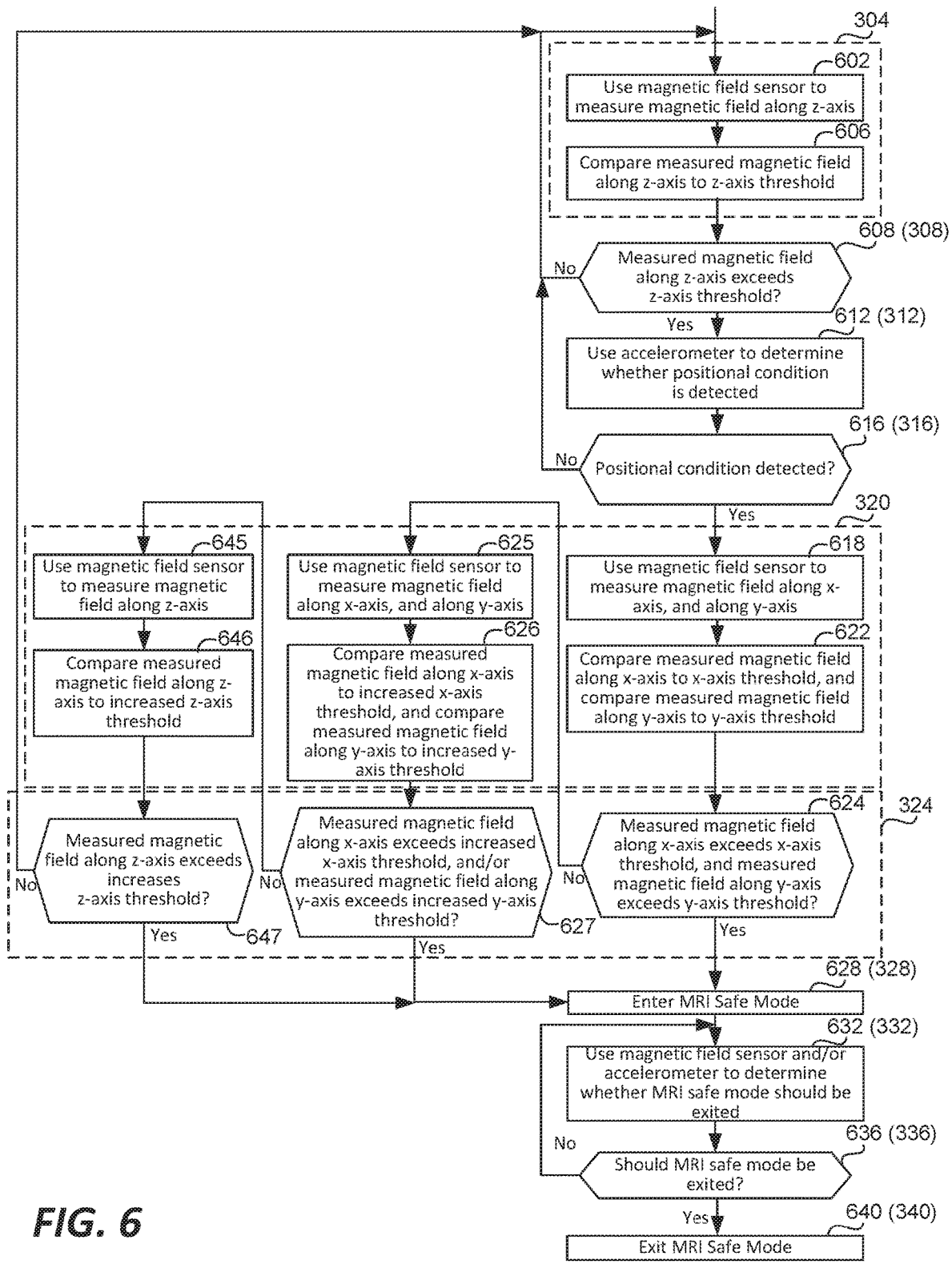
FIG. 6 is a high level flow diagram that is used to provide additional details of the methods introduced with reference to FIG. 3, according to still other embodiments of the present technology.

FIG. 6 will now be used to describe embodiments that can be used where the magnetic field sensor of the IMD is a three-axis magnetic field sensor (which as noted above, can also be referred to as a 3D magnetic field sensor), which can measure magnetic fields along a z-axis, an x-axis and a y-axis, which axes are explained above.

Referring to FIG. 6, step 602 involves using the magnetic field sensor to measure a magnetic field along the z-axis, step 604 involves comparing the measured magnetic field along the z-axis to a z-axis magnetic field threshold, and step 606 involves determining whether the measured magnetic field along the z-axis exceeds the z-axis magnetic field threshold. As can be appreciated by the dashed-block labeled 304, steps 602 and 604 shown therein are a specific implementation of step 304 in FIG. 3. Additionally, step 606 is a specific implementation of step 308 in FIG. 3. Further, as can be appreciated by comparing FIG. 6 to FIG. 4, steps 602, 604, and 606 in FIG. 6 are the same, respectively, as steps 402, 404, and 406 in FIG. 4. As can be appreciated by comparing FIG. 6 to FIG. 5, steps 602, 604, and 606 in FIG. 5 are also the same, respectively, as steps 502, 504, and 506 in FIG. 5.

Steps 612 and 616 in FIG. 6 (which are, respectively, specific implementations of steps 312 and 316 in FIG. 3) are the same as steps 412 and 416 in FIG. 4 (and the same as steps 512 and 516 in FIG. 5), and thus, need not be described in great detail again. In accordance with certain embodiments, the positional condition being monitored for at these steps is the patient being in a supine position. In accordance with other embodiments, the positional condition is the patient both being in a supine position and being stationary. In still other embodiments, the positional condition is the patient being stationary. In other words, in certain embodiments the accelerometer is used at step 612 to determine whether a patient is in a supine position (which is the position the patient will be when lying down in an MRI system, which can also be referred to as an MRI scanner), and/or the accelerometer can also be used at step 612 to determine whether the patient is stationary (which is how the patient will be instructed to be when lying down in an MRI system).

Still referring to FIG. 6, step 618 involves using the magnetic field sensor to measure the magnetic field along the x-axis, and using the magnetic field sensor to measure the magnetic field along the y-axis. Step 622 involves comparing the measured magnetic field along the x-axis to an x-axis magnetic field threshold, and comparing the measured magnetic field along the y-axis to a y-axis magnetic field threshold. Step 624 involves determining whether the measured magnetic field along the x-axis exceeds the x-axis magnetic field threshold, and determining whether the measured magnetic field along the y-axis exceeds the y-axis magnetic field threshold.

If the answer to the determination at step 624 is yes (i.e., if the measured magnetic field along the x-axis exceeds the x-axis magnetic field threshold, and the measured magnetic field along the y-axis exceeds the y-axis magnetic field threshold), then flow goes to step 628. Steps 628, 632, 636, and 640 are the same, respectively, as steps 328, 332, 336 and 340 described above with reference to FIG. 3, and thus, need not be described again.

If the answer to the determination at step 624 is no (i.e., if the measured magnetic field along the x-axis does not exceed the x-axis magnetic field threshold, and/or the measured magnetic field along the y-axis does not exceed the y-axis magnetic field threshold), then flow goes to step 625.

Step 625 involves using the magnetic field sensor to measure the magnetic fields along the x-axis and along the y-axis. Step 626 involves comparing the measured magnetic field along the x-axis to an increased x-axis magnetic field threshold, and comparing the measured magnetic field along the y-axis to an increased y-axis magnetic field threshold. Step 627 involves determining whether the measured magnetic field along the x-axis exceeds the increased x-axis magnetic field threshold, and determining whether the measured magnetic field along the y-axis exceeds the increased y-axis magnetic field threshold. The answer to step 627 can be yes because the measured magnetic field along the x-axis exceeds the increased x-axis magnetic field threshold, or it can be yes because the measured magnetic field along the y-axis exceeds the increased y-axis magnetic field threshold, or because both the increased x-axis magnetic field threshold and the increased y-axis magnetic field threshold are exceeded. The increased x-axis magnetic field threshold (used at step 625) can be, e.g., a margin or percentage greater than the x-axis magnetic field threshold (used at step 622). Similarly, the increased y-axis magnetic field threshold (used at step 625) can be, e.g., a margin or percentage greater than the y-axis magnetic field threshold (used at step 622). If the values of the magnetic fields measured along the x-axis and y-axis at step 618 were saved (e.g., in memory or a register), then step 625 can be skipped and the saved values (determined at step 618) can be used to perform the comparison at step 626. However, if steps 618 and 622 are performed substantially simultaneously and simply produce a binary answer, then the magnetic fields along the x-axis and the y-axis will need to be measured again at step 625.

If the answer to the determination at step 627 is yes, then flow goes to step 628. If the answer to the determination at step 627 is no (i.e., if the measured magnetic field along the x-axis does not exceed the increased x-axis magnetic field threshold, and the measured magnetic field along the y-axis does not exceed the increased y-axis magnetic field threshold), then flow goes to step 645. Steps 628, 632, 636, and 640 are the same, respectively, as steps 328, 332, 336 and 340 described above with reference to FIG. 3, and thus, need not be described again.

Still referring to FIG. 6, step 645 involves using the magnetic field sensor to measure the magnetic field along the z-axis, and step 645 involves comparing the measured magnetic field along the z-axis to an increased z-axis magnetic field threshold, and step 647 involves determining whether the measured magnetic field along the z-axis exceeds the increased z-axis magnetic field threshold. The increased z-axis magnetic field threshold (used at step 646) can be, e.g., a margin or percentage greater than the z-axis magnetic field threshold (used at step 606). If the value of the magnetic field measured along the z-axis at step 602 was saved (e.g., in memory or a register), then step 645 can be skipped and the saved value (determined at step 602) can be used to perform the comparison at step 646. However, if steps 602 and 606 are performed substantially simultaneously and simply produce a binary answer, then the magnetic field along the z-axis will need to be measured again at step 645.

As can be appreciated by the dashed-block labeled 320, steps 618 and 622, steps 625 and 626, and steps 645 and 646, shown therein are a specific implementation of step 320 in FIG. 3. Additionally, steps 624, 627 and 647 are a specific implementation of step 324 in FIG. 3. In the embodiments described with reference to FIG. 6, an MRI safe mode may be entered when measured magnetic fields along three axes all exceed respective first thresholds, or when the measured magnetic field along a single axis exceeds an increased threshold (which is greater than its respective first threshold).

If the answer to the determination at step 647 is no (i.e., if the measured magnetic field along the z-axis does not exceed the increased z-axis magnetic field threshold) then flow goes back to step 602.

In accordance with certain embodiments, the various methods summarized with reference to FIGS. 3 through 6 will only be initiated by an IMD if the IMD has been placed in an MRI ready mode. In order for an IMD to be placed in an MRI ready mode, a physician or clinician may need to perform traditional lead and other device checks to verify that the patient and device are safe to undergo an MRI. Such checks can involve ensuring that one or more cardiac pacing threshold(s) is/are within recommended ranges (where applicable), ensuring that lead impedance of lead nodes are within recommended ranges (where applicable), and ensuring that no foreign object in the patient will affect the MRI scan safety. The MRI ready mode may time out after a specified period, e.g., two weeks, but not limited thereto. In accordance with certain embodiments, if the IMD is within the MRI safe mode when the MRI ready mode times out, the IMD will be automatically switched from the MRI safe mode back to its normal mode of operation.

Further, prior to the various methods summarized with reference to FIGS. 3 through 6 being initiated by an IMD, either at implant or follow-up, a physician or clinician may enable posture detection and motion detection. For example, this can include calibrating an accelerometer (e.g., 221) to correctly identify when a patient is supine (i.e., lying down) or in an upright setting position. Additionally, this can include calibrating the accelerometer (e.g., 221) to obtain baseline motion data when the patient is stationary, and more specifically, lying down still.

In accordance with certain embodiments, the sampling rate of the magnetic field sensor (e.g., 219) can be adjusted based on whether the patient is supine and/or stationary, as detected using an accelerometer (e.g., 221). For example, when it is determined that the patient is upright and/or moving (and thus, is not likely within or otherwise exposed to an MRI system) the sampling rate of the magnetic field sensor (used to perform instances of step 304) can be relatively low to conserve power. By contrast, when it is determined that the patient is supine and stationary (and thus, potentially within or otherwise exposed to an MRI system) the sampling rate of the magnetic field sensor (used to perform instances of step 304) can be relatively high. Further the thresholds used at instances of step 304 (and more specifically, instances of steps 406, 506, or 606) can be set relatively high, and thereby provide a relatively low sensitivity, when it is determined that the patient is upright and/or moving (and thus, not likely within or otherwise exposed to an MRI system). By contrast, when it is determined that the patient is supine and stationary (and thus, potentially within or otherwise exposed to an MRI system), the threshold used at instances of step 304 (and more specifically, instances of steps 406, 506, or 606) can be reduced to thereby increase the sensitivity. Additional variations are also possible. For example, one or more intermediate magnetic field thresholds can be used when the patient is upright but stationary, and/or when the patient is supine but not stationary.

In accordance with certain embodiments, the threshold used at instances of step 304 (and more specifically, the z-axis threshold used at instances of steps 406, 506 and 606) is set relatively low, compared to the threshold(s) used at instances of step 320 (and more specifically, at instances of steps 422, 522 and 622) in order to reliably detect a magnetic field when the patient may be inside or near an MRI system.

In the above described embodiments, the potential positional condition that is monitored for using an accelerometer (e.g., at steps 312 and 316) was described as the patient being supine, or the patient being stationary, or the patient being both supine and stationery. In alternative embodiments, which can be used with upright MRIs, the potential positional condition that is monitored for using an accelerometer (e.g., at steps 312 and 316) can be the patient being upright, or the patient being stationary, or the patient being both upright and stationery.

Embodiments of the present technology describe above generally pertain to IMDs, and methods for use therewith, that can be used to automatically switch an IMD from its normal operational mode to an MRI safe mode, and vice versa, within increased specificity. Such embodiments of the present technology have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed technology. For example, it would be possible to combine or separate some of the steps shown in FIGS. 4 through 6. For another example, it is possible to change the boundaries of some of the blocks shown in FIG. 2.

The previous description of the preferred embodiments is provided to enable any person skilled in the art to make or use the embodiments of the present technology. While the technology has been particularly shown and described with reference to preferred embodiments thereof, it will be understood by those skilled in the art that various changes in form and details may be made therein without departing from the spirit and scope of the technology.

What is claimed is:

1. A method for use with an implantable medical device (IMD) that is implanted within a patient, wherein the IMD includes a magnetic field sensor and an accelerometer and is capable of mode switching to a magnetic resonance imaging (MRI) safe mode, the method comprising:
   (a) using the magnetic field sensor to determine whether a first magnetic field condition is detected;
   (b) in response to determining that the first magnetic field condition is detected, using the accelerometer to determine whether a positional condition is detected;
   (c) in response to determining that the positional condition is detected, using the magnetic field sensor to determine whether a second magnetic field condition is detected, wherein the second magnetic field condition differs from the first magnetic field condition; and
   (d) performing a mode switch to the MRI safe mode, based at least in part on determining that the first and second magnetic field conditions and the positional condition are detected;
   wherein the first magnetic field condition comprises a measured magnetic field along a first-axis exceeding a first-axis threshold; and
   wherein the second magnetic field condition comprises a measured magnetic field along a second-axis, which is orthogonal to the first-axis, exceeding a second-axis threshold.

2. The method of claim 1, wherein:
   the positional condition comprises the patient being supine; and
   step (b) comprises, in response to determining that the first magnetic field condition is detected, using the accelerometer to determine whether the patient is supine.

3. The method of claim 1, wherein:
   the positional condition comprises the patient being both supine and stationary; and
   step (b) comprises, in response to determining that the first magnetic field condition is detected, using the accelerometer to determine whether the patient is both supine and stationary.

4. The method of claim 1, wherein the magnetic field sensor is selected from the group consisting of:
   at least one Hall effect sensor;
   at least one giant magnetoresistance (GMR) sensor; or
   at least one reed switch.

5. The method of claim 1, wherein:
   step (a) includes sampling the magnetic field sensor or at least one signal output therefrom at a first sampling frequency; and
   step (c) includes sampling the magnetic field sensor or at least one signal output therefrom at a second sampling frequency that is greater than the first sampling frequency.

6. The method of claim 1, wherein:
   step (a) comprises using the magnetic field sensor to determine whether the measured magnetic field along the first-axis exceeds the first-axis threshold;
   step (b) comprises, in response to determining that the measured magnetic field along the first-axis exceeds the first-axis threshold, using the accelerometer to determine whether the positional condition is detected;
   step (c) comprises, in response to determining that the positional condition is detected, using the magnetic field sensor to determine whether the measured magnetic field along the second-axis exceeds the second-axis threshold; and
   step (d) comprises performing the mode switch to the MRI safe mode, based at least in part on determining at step (a) that the measured magnetic field along the first-axis exceeds the first-axis threshold, determining at step (b) that the positional condition is detected, and determining at step (c) that the measured magnetic field along the second-axis exceeds the second-axis threshold.

7. The method of claim 6, further comprising:
   (e) in response to determining at step (c) that the measured magnetic field along the second-axis does not exceed the second-axis threshold, using the magnetic field sensor to determine whether a measured magnetic field along the first-axis exceeds an increased first-axis threshold; and
   (f) performing a mode switch to the MRI safe mode, based at least in part on determining at step (a) that the measured magnetic field along the first-axis exceeds the first-axis threshold, determining at step (b) that the positional condition is detected, and determining at step (e) that the measured magnetic field along the first-axis exceeds the increased first-axis threshold.

8. The method of claim 1, wherein:
   the second magnetic field condition comprises also a measured magnetic field along a third-axis exceeding a third-axis threshold, the first-, second-, and third-axes being orthogonal to one another;
   step (a) comprises using the magnetic field sensor to determine whether the measured magnetic field along the first-axis exceeds the first-axis threshold;
   step (b) comprises, in response to determining that the measured magnetic field along the first-axis exceeds the first-axis threshold, using the accelerometer to determine whether the positional condition is detected;
   step (c) comprises, in response to determining that the positional condition is detected, using the magnetic field sensor to determine whether the measured magnetic field along the second-axis exceeds the second-axis threshold, and using the magnetic field sensor to determine whether the measured magnetic field along the third-axis exceeds the third-axis threshold; and step (d) comprises performing the mode switch to the MRI safe mode, based at least in part on determining at step (a) that the measured magnetic field along the first-axis exceeds the first-axis threshold, determining at step (b) that the positional condition is detected, and determining at step (c) that the measured magnetic fields along the second-axis and the third-axis respectively exceed the second-axis threshold and the third-axis threshold.

9. The method of claim 8, further comprising:

(e) in response to determining at step (c) that the measured magnetic field along the second-axis does not exceed the second-axis threshold and/or that the measured magnetic field along the third-axis does not exceed the third-axis threshold, using the magnetic field sensor to determine whether a measured magnetic field along at least one of the first-, second- or third-axis exceeds a respective increased first-, second- or third-axis threshold; and (f) performing a mode switch to the MRI safe mode, based at least in part on determining at step (a) that the measured magnetic field along the first-axis exceeds the first-axis threshold, determining at step (b) that the positional condition is detected, and determining at step (e) that the measured magnetic field along at least one of the first-, second- or third-axis exceeds the respective increased first-, second- or third-axis threshold.

10. A method for use with an implantable medical device (IMD) having a magnetic field sensor and an accelerometer capable of mode switching to a magnetic resonance imaging (MRI) safe mode, the method comprising:

(a) using the magnetic field sensor to determine whether a first magnetic field condition is detected;

(b) in response to determining that the first magnetic field condition is detected, using the accelerometer to determine whether a positional condition is detected;

(c) in response to determining that the positional condition is detected, using the magnetic field sensor to determine whether a second magnetic field condition is detected, wherein the second magnetic field condition differs from the first magnetic field condition; and (d) performing a mode switch to the MRI safe mode, based at least in part on determining that the first and second magnetic field conditions and the positional condition are detected; wherein:

the first magnetic field condition comprises a measured magnetic field along a first-axis exceeding a first-axis threshold;

the second magnetic field condition comprises a measured magnetic field along the first-axis exceeding an increased first-axis threshold;

step (a) comprises using the magnetic field sensor to determine whether the measured magnetic field along the first-axis exceeds the first-axis threshold;

step (b) comprises, in response to determining that the measured magnetic field along the first-axis exceeds the first-axis threshold, using the accelerometer to determine whether the positional condition is detected;

step (c) comprises, in response to determining that the positional condition is detected, using the magnetic field sensor to determine whether the measured magnetic field along the first-axis exceeds the increased first-axis threshold; and step (d) comprises performing the mode switch to the MRI safe mode, based at least in part on determining at step (a) that the measured magnetic field along the first-axis exceeds the first-axis threshold, determining at step (b) that the positional condition is detected, and determining at step (c) that the measured magnetic field along the first-axis exceeds the increased first-axis threshold.

11. An implantable medical device (IMD), comprising:
a magnetic field sensor;
an accelerometer; and
a controller configured to
use the magnetic field sensor to determine whether a first magnetic field condition is detected;
use the accelerometer to determine whether a positional condition is detected;
use the magnetic field sensor to determine whether a second magnetic field condition is detected, in response to both the first magnetic field condition being detected and the positional condition being detected, wherein the second magnetic field condition differs from the first magnetic field condition; and
cause the IMD to enter a magnetic resonance imaging (MRI) safe mode based at least in part on the first and second magnetic field conditions and the positional condition being detected; and
wherein the first magnetic field condition comprises a measured magnetic field along a first-axis exceeding a first-axis threshold; and
wherein the second magnetic field condition comprises a measured magnetic field along the first-axis exceeding an increased first-axis threshold.

12. The method of claim 11, wherein the positional condition comprises the patient being both supine and stationary.

13. The IMD of claim 11, wherein:
the second magnetic field condition also comprises a measured magnetic field along a second-axis, which is orthogonal to the first-axis, exceeding a second-axis threshold.

14. The IMD of claim 11, wherein:
the second magnetic field condition also comprises a measured magnetic field along a second-axis exceeding a second-axis threshold, and a measured magnetic field along a third-axis exceeding a third-axis threshold, wherein the first-, second-, and third-axes are orthogonal to one another.

15. An implantable medical device (IMD), comprising:
a magnetic field sensor capable of measuring magnetic fields along more than one axes;
an accelerometer capable of detecting posture of a patient within which the IMD is implanted and capable of detecting motion of the patient; and
a controller configured to
use the magnetic field sensor to detect when a magnetic field along a first-axis exceeds a first-axis threshold;
use the accelerometer to detect when a patient is supine and stationary; and
use the magnetic field sensor to detect when a magnetic field along a second-axis exceeds a second-axis threshold, wherein the second-axis is orthogonal to the first-axis;
the controller also configured to cause the IMD to enter a magnetic resonance imaging (MRI) safe mode based at least in part on the magnetic field sensor being used to detect that magnetic field along the first-axis exceeds the first-axis threshold, the accelerometer being used to detect that the patient is supine and stationary, and the magnetic field sensor being used to detect that magnetic field along the second-axis exceeds the second-axis threshold.

16. The IMD of claim 15, wherein the controller is also configured to:

use the magnetic field sensor to detect when a magnetic field along a third-axis exceeds a third-axis threshold, wherein the third-axis is orthogonal to the first- axis and the second-axis; and cause the IMD to enter the MRI safe mode based at least in part on the magnetic field sensor being used to detect that magnetic field along the first-axis exceeds the first-axis threshold, the accelerometer being used to detect that the patient is supine and stationary, and the magnetic field sensor being used to detect that magnetic field along the second-axis exceeds the second-axis threshold, and the magnetic field along the third-axis exceeds the third-axis threshold.

17. The IMD of claim 15, wherein the IMD is configured to deliver pacing pulses to the heart of the patient within which the IMD is implanted, and wherein:

a normal operational mode of the IMD comprises one of a DDDR, DDD, DDI, or DVI mode, and the MRI safe mode comprises a DOO mode;

a normal operational mode of the IMD comprises one of a VDDR, VDD, VDI, or VVI mode, the MRI safe mode comprises a VOO mode; or a normal operational mode of the IMD comprises one of an ADDR, ADD, ADI, or AVI mode, the MRI safe mode comprises an AOO mode.

18. The IMD of claim 17, wherein the controller is also configured to cause the IMD to exit the MRI safe mode and return to the normal operational mode of the IMD.

19. The IMD of claim 15, wherein the controller is configured to cause:

measurements of the magnetic field along the first-axis to be obtained using a first sampling frequency; and measurements of the magnetic field along the second-axis to obtained using a second sampling frequency, which is greater than the first sampling frequency, in response to the controller detecting, using the magnetic field sensor, that the magnetic field along the first-axis exceeds the first-axis threshold, and the controller detecting, using the accelerometer, that the patient is supine and stationary.

* * * * *